United States Patent
Bausewein et al.

(10) Patent No.: US 7,922,378 B2
(45) Date of Patent: Apr. 12, 2011

(54) MEDICAL ILLUMINATION UNIT

(75) Inventors: Markus Bausewein, Aalen (DE); Michael J. Eichler, Aalen (DE)

(73) Assignee: Carl Zeiss Surgical GmbH (DE)

( * ) Notice: Subject to any disclaimer, the term of this patent is extended or adjusted under 35 U.S.C. 154(b) by 146 days.

(21) Appl. No.: 12/270,923

(22) Filed: Nov. 14, 2008

(65) Prior Publication Data

US 2009/0129051 A1  May 21, 2009

(30) Foreign Application Priority Data

Nov. 14, 2007  (DE) .......................... 10 2007 055 003

(51) Int. Cl.
*A61B 1/06* (2006.01)
*F21S 4/00* (2006.01)

(52) U.S. Cl. ........ 362/572; 362/573; 362/555; 362/574; 362/575

(58) Field of Classification Search ................... 362/551, 362/555, 572, 573, 574, 575, 34
See application file for complete search history.

(56) References Cited

U.S. PATENT DOCUMENTS

| | | | |
|---|---|---|---|
| 5,445,608 A * | 8/1995 | Chen et al. ....................... 604/20 |
| 6,028,694 A | 2/2000 | Schmidt |
| 6,068,383 A | 5/2000 | Robertson et al. |
| 6,466,135 B1 * | 10/2002 | Srivastava et al. .......... 340/815.4 |
| 6,504,301 B1 * | 1/2003 | Lowery ......................... 313/512 |
| 6,577,073 B2 * | 6/2003 | Shimizu et al. ................ 315/246 |
| 6,711,426 B2 * | 3/2004 | Benaron et al. ................ 600/342 |
| 6,903,380 B2 | 6/2005 | Barnett et al. |
| 7,005,679 B2 * | 2/2006 | Tarsa et al. ...................... 257/89 |
| 7,138,667 B2 | 11/2006 | Barnett et al. |
| 2004/0090796 A1 * | 5/2004 | Steen et al. ..................... 362/572 |
| 2004/0135158 A1 | 7/2004 | Hon |
| 2004/0150991 A1 * | 8/2004 | Ouderkirk et al. ............ 362/231 |
| 2005/0154262 A1 | 7/2005 | Banik et al. |
| 2005/0194876 A1 | 9/2005 | Shimada et al. |
| 2006/0069314 A1 | 3/2006 | Farr |
| 2006/0245702 A1 | 11/2006 | Cazzini |
| 2006/0266366 A1 | 11/2006 | Tsukashima et al. |
| 2006/0291195 A1 | 12/2006 | Horrell et al. |
| 2007/0018177 A1 | 1/2007 | Lee et al. |

FOREIGN PATENT DOCUMENTS

DE  101 42 009 A1  3/2003
WO  20061102846 A1  10/2006

* cited by examiner

*Primary Examiner* — Sandra L O Shea
*Assistant Examiner* — Danielle Allen
(74) *Attorney, Agent, or Firm* — Gerald E. Hespos; Michael J. Porco

(57) ABSTRACT

A medical illumination unit (1) has an LED chip (15) and a rod-shaped body (5) with a proximal end (11) and a distal end (7). A distal hollow section (9) begins before the distal end (7) and reaches the distal end (7), and a supply lead section (12) begins at the proximal end (11) and reaches the distal hollow section (9). The LED chip (15) is in the distal hollow section of the rod-shaped body (5) and is supplied with energy through the supply lead (12). A luminescent converter is between the LED chip (15) and the distal end (7) of the rod-shaped or tubular body or at the distal end of the rod-shaped body (5), the converter properties of which are selected to convert light emitted by the LED chip (15) into light with a desired wavelength distribution.

15 Claims, 4 Drawing Sheets

MEDICAL ILLUMINATION UNIT

BACKGROUND OF THE INVENTION

1. Field of the Invention

The present invention relates to a medical illumination unit having a rod-shaped body, which has a proximal end and a distal end and which can be inserted into a small-dimensioned opening.

2. Description of the Related Art

Medical illumination devices of this generic type are used in particular as so-called endo-illuminators, which are employed in operations in which the illumination should be brought very close to the operation site and/or should be introduced inside the body. Endo-illuminators are important particularly in the scope of minimally invasive operations. For example in opthalmology, the interior of the eye is often illuminated through a small incision with the aid of the thin light guide of an endo-illuminator.

A medical illuminator, by which the interior of the eye can be illuminated and which comprises a thin cannula arranged on a handpiece for introduction into the eye, is described for example in EP 1 719 482 A1. In the illuminator described therein, light from a light source is guided to the distal end of the cannula by means of a light guide extending through the cannula. At the proximal end of the cannula, a handpiece is provided from which the light guide is extended to a stationary light source.

US 2004/0090796 A1 describes a light source for use in opthalmology, in which the light source is arranged in the handpiece instead of in an external unit. An LED is employed as the light source, the light of which is injected through a lens into the proximal end of needle-like fiber optics. The injected light is guided by the needle to the distal end. The distal end of the needle can be inserted into the eye through a small opening, in order to illuminate the eye from the inside. US 2004/0090796 A1 furthermore describes another alternative embodiment in which the LED is arranged inside the needle, shortly before its distal end. An electrical supply lead is fed through the needle to the LED. This document does not, however, describe the way in which this configuration should specifically be embodied. In particular, the document does not reveal how an LED can be arranged in the very restricted interior of the needle.

It is therefore an object of the present invention to provide a medical illumination unit which comprises a rod-shaped body having a proximal end and a distal end, the light source being arranged in the region of the distal end, and which can also be produced with a small dimensions of the rod-shaped body.

SUMMARY OF THE INVENTION

A medical illumination unit according to the invention comprises an LED chip and a rod-shaped body, which comprises a proximal end and a distal end. The rod-shaped body furthermore comprises at least one distal hollow section which begins before the distal end and reaches to the distal end, and a supply lead section which begins at the proximal end and reaches to the distal hollow section. The distal hollow section may in particular also begin at the proximal end of the rod-shaped body, so that the distal hollow section and the supply lead section are formed by the same section. The LED chip is arranged in the distal hollow section of the rod-shaped body, and is supplied with energy through the supply lead section. A lead in this case may be routed through the supply lead section of the rod-shaped body. As an alternative, the rod-shaped body itself may also be designed as an electrical lead. In the medical illumination unit according to the invention, a luminescent converter material is arranged between the LED chip and the distal end of the rod-shaped body or at the distal end itself. The converter properties of the luminescent converter material are selected in respect of the light emitted by the LED chip so that it converts the light emitted by the LED chip into light with a desired wavelength distribution, for example into white light.

The invention is based on the following concepts:

In medical illumination devices, white light is conventionally intended to be employed as illumination light. White LEDs, however, are based not on a chip which emits white light but on a chip which emits blue or ultraviolet light and whose light is converted into white light by a converter material applied on the LED chip. Applying the converter material on the LED chip increases its dimensions compared to an LED chip without converter material. By separating the LED chip and the converter material, the limitedly available space in the distal hollow section of a thin rod-shaped border is utilized better than when the LED chip and the converter material form a unit.

In the medical illumination unit according to the invention, it is possible first to contact the LED chip with the electrical supply lead and only then to arrange the converter material between the LED chip and the distal end of the rod-shaped body or at the distal end itself. In this way, the contacting and positioning of the LED chip are not hindered by a converter material previously applied on the chip. The increased flexibility thereby obtained for contacting and positioning the LED chip facilitates its installation in the distal hollow section of a thin rod-shaped body. Furthermore, the LED chip also has smaller dimensions during installation than a completed LED, which is already enclosed by a converter material. This also increases the flexibility when positioning the LED chip and when arranging the contacts for contacting the LED chip.

In a first specific alternative embodiment of the medical illumination unit according to the invention, the luminescent converter material encloses the LED chip in the form of encapsulation. This is applied after positioning and contacting the LED chip, and may in particular also cover the contacts. This provides the opportunity to bring the contacts closer to the LED chip than would be possible with a completed LED, i.e. if the LED chip were enclosed by a converter material in advance. Furthermore, the available space can be filled optimally with converter material during the encapsulation, which would not be readily possible for a predetermined geometry of a completed LED.

In an alternative variant of a specific configuration of the medical illumination unit, the rod-shaped body is sealed at its distal end with a transparent plate onto which the luminescent converter material is applied or into which the luminescent converter material is introduced. The luminescent converter material may, for example, be applied onto the plate in the form of a film or a coating, in which case the film or the coating may in principle be applied on the inside or the outside of the plate. In particular, it is also possible to apply the film or the coating both on the outside and on the inside. It is, however, particularly advantageous for the film or the coating to be arranged only on the inside of the plate, i.e. that side of the plate which faces the interior of the distal hollow section, since the biocompatibility of the converter material does not then need to be taken into account and the film is protected against body fluids if the distal hollow section is sealed sufficiently.

When using a film for the conversion, the film material itself may be the luminescent converter material, or the luminescent converter material may be introduced into a film material as carrier material.

If the luminescent converter material is introduced into the plate, this may be done by doping. The same naturally applies when the converter material is introduced into a carrier film.

In the medical illumination unit according to the invention, the supply lead section may comprise a contact arrangement at its end facing the distal hollow section, having a first contact and a second contact for the LED chip. The LED chip is then arranged on the first contact so that it contacts it, and is connected to the second contact by a bonding wire. This type of contacting requires only little space, since it is merely necessary to provide one bonding wire. The electrical contact of the LED chip with the first contact may be made by means of so-called die bonding, in which a chip is directly applied electrically conductively onto a substrate without a housing.

In relation to the supply lead section, the first contact may be a central contact and the second contact an edge contact. This configuration has the advantage that the LED chip, which is in fact applied on the first contact while contacting it, is arranged on the mid-axis of the rod-shaped body, which proves to be particularly advantageous when emission is intended to be carried out symmetrically with respect to the mid-axis of the rod-shaped body. If the edge contact furthermore encloses the central contact in the form of a ring, then the orientation of the bonding wire may be selected freely in relation to the radial direction of the rod-shaped body, which increases the latitude for orienting the LED chip.

In a particular configuration of the alternative embodiment with a central contact and an annular edge contact, the edge contact projects beyond the central contact in the direction of the distal end of the rod-shaped body. The edge contact also encloses the central contact without a gap, electrical insulation being provided between the edge contact and the central contact. In this configuration, the central contact forms a recess which is enclosed by the edge contact and may serve as a holder for converter material. The converter material may in this case be introduced as encapsulation into the recess. It is however also possible to introduce a powdered converter material into the recess, and subsequently fix it in the recess by a suitable treatment, for example by means of a suitable curing method. In principle, however, it is also possible to fix for instance a liquid or powdered converter material mechanically by means of a plate which tightly seals the recess. The electrical insulation between the central contact and the edge contact may, in particular, be produced by an adhesive bond with an electrically insulating adhesive.

The distal hollow section of the medical illumination unit need not be designed integrally with the other sections of the rod-shaped body. It is also possible for the distal hollow section to be formed by a cylindrical sleeve, into which the LED chip is introduced and which is fitted onto the supply lead section of the rod-shaped body. The LED chip may then initially be inserted into the sleeve before the latter is fitted onto the distal end of the supply lead section. In particular, in this case it is possible first to connect the LED chip to contacts of the supply lead section and optionally encapsulate the LED, before the sleeve is fitted over the LED. The converter encapsulation in this alternative embodiment may already be cured when the sleeve is fitted on, so that in principle there is no reason why the sleeve should not be fitted on in such a way that it contacts the converter encapsulation with a front plate arranged on the distal end, so that reproducibility of the positioning of the LED chip can readily be achieved in the production process for the medical illumination unit. The contact arrangement described above may in this case form a base, onto which the sleeve is fitted.

The supply lead section of the rod-shaped body may, in particular, be designed as a small tube, through which an electrical lead is fed to the LED chip. The distal hollow section may also be formed integrally with the small tube of the supply lead section in this case, so that the number of parts is reduced. Furthermore, the outer surface of the rod-shaped body then comprises no joints, which increases the sterilizability of the rod-shaped body.

In particular, a flexible conductor strip may be employed as the electrical lead. This configuration provides the opportunity to make an end of the conductor strip, projecting from the proximal end of the supply lead section, wider than the conductor strip inside the small tube. This simplifies connection of the conductor strip projecting from the small tube to an electrical supply unit.

When the supply lead section has a contact arrangement on its end facing the distal hollow section, with a first contact and a second contact for the LED chip, and the LED chip is arranged on the first contact while contacting it and is connected to the second contact through a bonding wire, the conductor strip may comprise a first electrical contacting section and a second electrical contacting section. The first contact is then designed as a first electrically conductive block connecting with the first contacting section of the conductor strip. The second contact is designed as a second electrically conductive block connecting with the second contacting section of the conductor strip, which is electrically insulated from the first electrically conductive block. In this way, the first electrically conductive block and the second electrically conductive block can be shaped and connected together so that together they form an electrical base element. The option is furthermore available to apply the encapsulation onto the cylindrical base element while covering the LED chip. The electrically conductive blocks in this configuration may be trimmed to size after connection to the conductor strip, which allows the base to be adapted particularly well to a cylindrical distal hollow section.

The medical illumination unit may also comprise a first and a second conductor strip, which each have a front side and a rear side, the front sides respectively having a first and a second electrical contacting section. The two conductor strips are then connected together rear side on rear side. An LED chip is respectively arranged on the front sides. In this configuration, a base for an LED chip is not necessary. By obviating the base, i.e. by manufacture merely in the form of flexible conductor strips onto which the LED chips are applied, this configuration is very compact. The brightness of the medical illumination unit is also increased by the two LED chips applied on the conductor strips arranged back to back, and this allows lateral emission of the light from the distal end of the rod-shaped body.

In another variant of the medical illumination unit, a flexible conductor strip is provided which comprises a first and a second electrical contacting section. The supply lead section of the rod-shaped body is furthermore designed as a small tube. The first electrical contacting section then forms the first contact of a contact arrangement, onto which the LED chip is directly applied electrically conductively. The second electrical contacting section, on the other hand, forms the second contact of the contact arrangement to which the LED chip is electrically conductively connected through a bonding wire. In this alternative embodiment, a rod with a flat distal end is furthermore provided, the diameter of which is less than the internal diameter of the small tube forming the supply lead section. The conductor strip bears in the region of its first electrical contacting section on the flat distal end of the rod. This variant provides the opportunity for the LED chip first to be applied onto the conductor strip and contacted by its contacting sections, before it is introduced into the distal hollow section of the rod-shaped body. It is also possible for converter encapsulation to be applied before introduction into the distal hollow section. The conductor strip may then be placed around the rod so that it bears on the flat distal end of the rod with the region in which the LED chip is arranged. In this configuration, the rod with the conductor strip placed around it may then be inserted into the sleeve forming the distal hollow section. This sleeve may, in particular, also form the entire rod-shaped body. If the LED chip is encapsulated when inserted into the sleeve, it may be inserted to a distance such that the converter encapsulation contacts a front plate on the distal end of the sleeve, which facilitates positioning the LED chip always in the same way.

The rod advantageously has a good thermal conductivity, for example by its being designed as a metal rod. A wire should also be regarded as a metal rod in this context, since the difference between a metal rod and a metal wire becomes unclear for very thin metal rods.

In all alternative embodiments, the LED chip may in particular also be encased by a sterilizable material, for example an epoxide, acrylate or silicone. This encasement may for example be produced by the rod-shaped body, when its walls are made of corresponding material.

Other features, properties and advantages of the present invention may be found in the following description of exemplary embodiments with reference to the appended figures.

DETAILED DESCRIPTION OF THE PREFERRED EMBODIMENTS

Figure 1:
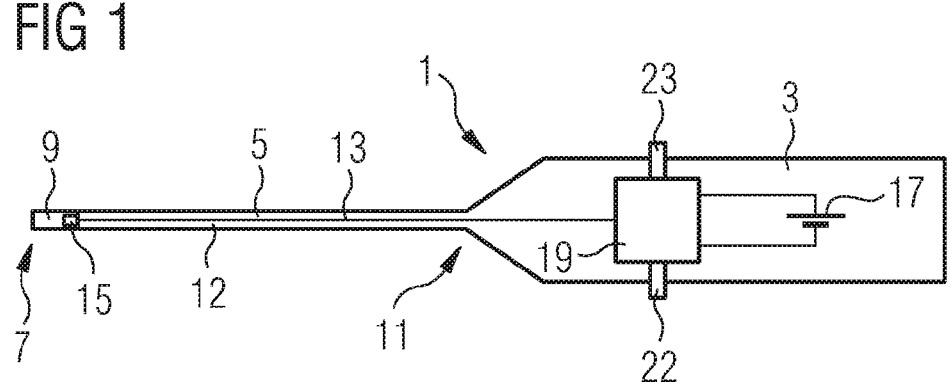
FIG. 1 shows an endo-illuminator in a highly schematized representation as an exemplary embodiment of the medical illumination unit according to the invention.

An endo-illuminator will be described below as an exemplary embodiment of a medical illumination unit according to the invention. The endo-illuminator 1 is shown in a highly schematized representation in FIG. 1. It comprises a handle 3 and a small tube or small rod 5 which extends from the handle 3, and which preferably has an external diameter of no more than 1 mm and preferably no more than 0.5 mm. The distal end of the small tube or small rod 5 may also have a tip, so that the small tube forms a needle.

At the distal end 7 of the small tube or small rod 5, a distal hollow section 9 is provided which begins before the distal end 7 and reaches as far as it. In the direction of the proximal end 11 of the small tube or small rod 5, a supply lead section 13 follows on from the distal hollow section 9. Through this supply lead section 13, in the embodiment of the endo-illuminator represented in FIG. 1, an electrical supply lead 15 is routed to the distal hollow section 9. A light-emitting diode chip (LED chip) is arranged in this distal hollow section, and is supplied with electrical power by the electrical lead 15.

In the region of the distal hollow section 9, the wall of the small tube or small rod 5 is at least partially transparent. Between the LED chip 15 and at least the transparent section of the wall of the distal hollow section 9, a converter material (not represented in FIG. 1) is arranged which converts the light emitted by the LED chip, referred to below as excitation radiation, at least partially into light of a longer wavelength.

An LED chip which emits blue, violet or ultraviolet light is typically employed as the LED chip 15. This is advantageous because light converted by luminescent converter materials always has a longer wavelength than the excitation light. The more shortwave the excitation radiation is, the greater is the wavelength range in the visible spectral range in which conversion can be carried out.

If for example the LED chip 15 emits a blue light and the luminescent converter material is selected so that a part of this blue light is converted into yellow light, then the light which results from superposition of the converted component of the excitation radiation and the unconverted component of the excitation radiation appears white. In this way, despite the use of an LED chip emitting blue, violet or ultraviolet light, white light is emitted by the endo-illuminator 1. When more than one converter material is provided, it is for example possible to convert parts of the excitation radiation into the light of different wavelengths, for example into green, yellow and red light. Together with an unconverted fraction of the excitation radiation, it is thus possible to achieve a broad and uniform wavelength distribution of the light emitted by the distal end 7 of the endo-illuminator 1.

In order to prevent damage to the tissue by unconverted excitation radiation, the wall of the distal hollow section may also be provided with a UV radiation blocking coating where it is transparent. As an alternative to a coating, a UV-blocking material may also be introduced into the transparent material of the distal hollow section 9, or the transparent material itself is opaque to UV.

The supply lead section 12 in the present example is designed as a small tube, through which the electrical lead 13 is fed to the distal hollow section 9. The handle 3 in the present exemplary embodiment contains a battery, which is represented as a voltage source 17 in FIG. 1 and by which the LED chip 15 is provided with electrical power. Electronics 19, which for example can be actuated by buttons 21, 23 for instance in order to switch the endo-illuminator 1 on and off or control its brightness, are arranged between the battery 17 and the electrical lead 13. Instead of buttons, of course, it is possible to provide other operating elements, for example sliders, small wheels, etc.

Although the supply lead section 12 is designed as a small tube in the present exemplary embodiment, it may also be designed as a small rod. In this case, the small rod is composed of two components which are electrically insulated from one another. These two components are then used as electrical supply leads for the LED chip 15. Such a small rod may also be enclosed by an insulating layer. This layer is preferably highly biocompatible and sterilizable. If the layer is transparent for the visible light, then it may also enclose the distal hollow section 9 so that the layer forms a continuous layer for the entire small rod or small tube 5, i.e. including the supply lead section 12 and the distal hollow section 9.

Figure 2:
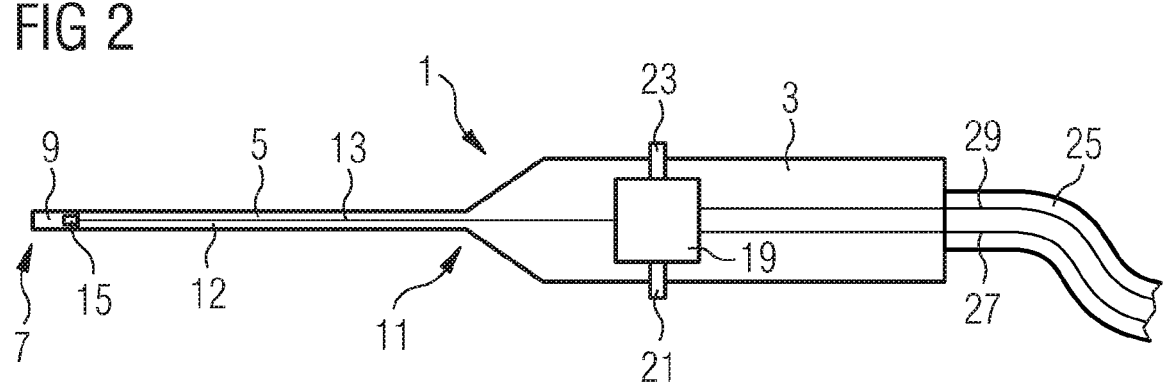
FIG. 2 shows a modification of the endo-illuminator represented in FIG. 1.

FIG. 2 shows an alternative variant of the endo-illuminator represented in FIG. 1. The endo-illuminator represented in FIG. 2 differs from the endo-illuminator represented in FIG.

1 merely in that instead of the battery compartment, it comprises a cable 25 through which electronic leads 27, 29 coming from the electronics 19 are fed to an external electricity supply. The other elements of the endo-illuminator represented in FIG. 2 correspond to those of the endo-illuminator represented in FIG. 1. They are therefore denoted by the same references as in FIG. 1 and will not be explained again.

Figure 3:
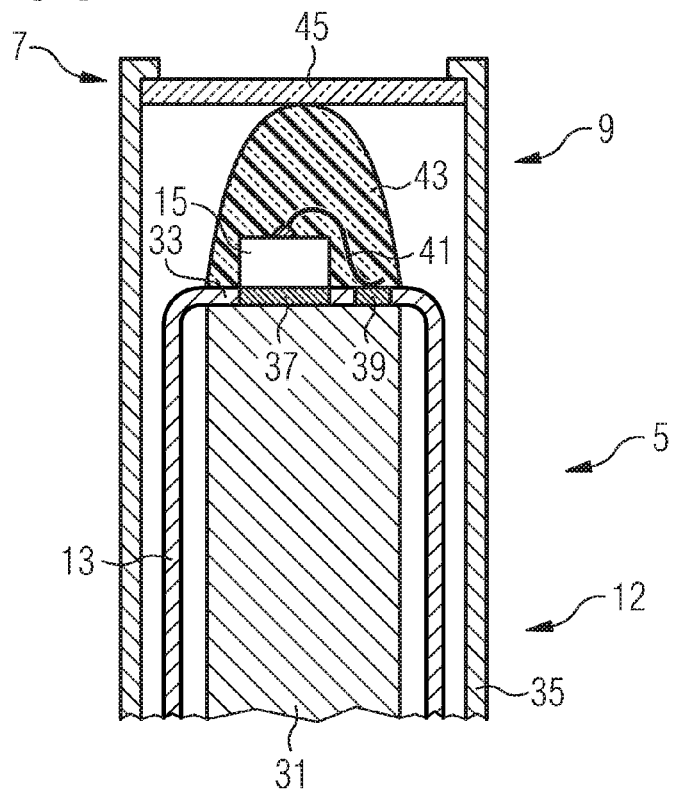
FIG. 3 shows the distal end of the endo-illuminator in FIG. 1 or FIG. 2.

FIG. 3 shows in detail the distal end of a first alternative embodiment of the small rod or small tube 5, which is designed as a small tube 35 in this alternative embodiment. The distal end 7, the distal hollow section 9 with an LED chip 15 arranged therein, as well as the supply lead section 12 with the electrical lead 13 extending therein, may be seen in the figure.

The electrical lead 13 in this alternative embodiment is configured as a flexible conductor strip, which is placed around a small rod 31 with a flattened distal end 33. The small rod 31 and the conductor strip 13 have their dimensions selected so that they can be inserted together into the small tube 35 when the conductor strip 13 is placed around the small rod 31.

In the region in which the conductor strip 13 bears on the flat distal section 33 of the small rod 31, a first electrical contact 37 and a second electrical contact 39 are arranged in the conductor strip 13. The LED chip 15 is applied onto the first electrical contact 37 while electrically contacting the contact 37. The LED chip 15 is connected to the second electrical contact 39, which is insulated from the first electrical contact, through a bonding wire 41.

The LED chip 15 and the bonding wire 41 are furthermore encased by encapsulation 43 applied on the conductor strip 13. In the present exemplary embodiment a converter material, which converts the excitation radiation coming from the LED chip 15 at least partially into light with a longer wavelength, as was described with reference to FIG. 1, is also mixed with the encapsulation 43. Of course, a plurality of different converter materials may also be mixed with the encapsulation 43. In principle, however, it is also possible for the encapsulation material itself to be a converter material.

The distal hollow section 9 is sealed at the distal end 7 of the small tube 135 by a plate 45. The plate 45 is transparent at least in the visible spectral range, but may also be transparent in the adjacent spectral ranges. It is however preferably opaque in the ultraviolet spectral range in order to block any ultraviolet radiation components of the LED chip 15, which have not been converted by the converter material.

Instead of in the encapsulation 43, the converter material may also be applied in or on the transparent plate 45. If it is applied on the transparent plate 45, it may be applied either in the form of a film or in the form of the coating. The film may either itself form the converter material or be used as a carrier material for a converter material introduced into the film. If the converter material is introduced into the film or the plate 45, this may be done in the form of doping. In principle, it is also possible to arrange a luminescent converter material both in the encapsulation 43 and in or on the plate 45. For example, the converter material of the plate 45 may in this case convert the excitation light into a different wavelength than the converter material of the encapsulation 43.

In the present exemplary embodiment, the plate 45 furthermore seals the distal hollow section 9 from the surroundings. This sealing function is however not necessary when the distal hollow section has a sealing coat, as was described with reference to FIG. 1.

In order to assemble the embodiment of the endo-illuminator represented in FIG. 3, and in particular the small rod or small tube 5, the LED chip 15 is first fitted onto the first contact 37 of the conductor strip 13 so that an electrically conductive connection is obtained, and the bonding connection with the second contact 39 is established. The arrangement is subsequently encapsulated. The encapsulation may be carried out on a flat support, so that the rear side of the conductor strip 13 constitutes a flat surface after the encapsulation and curing of the encapsulation. The conductor strip is subsequently placed with the encapsulated region onto the flat distal end 33 of the small rod 31, and fixed thereon for example by an adhesive bonding. The ends of the conductor strip 13 are then routed along this small tube 31 and optionally likewise adhesively bonded to it. The entire arrangement is then inserted into the small hollow tube 35. The insertion may be carried out to such an extent that the encapsulation 43 contacts the plate 45.

This alternative embodiment offers the advantage that the manufacture, up to and including application of the encapsulation 43, can be carried out with a flat conductor strip. In order to facilitate insertion of the arrangement comprising the small rod 31 and the conductor strip 13 with the LED chip 15 into the tube 35, the latter may be widened at the proximal end. The conductor strip 13 may also be widened in those regions by which it projects from the proximal end of the small tube 35, so that contacting with the electronics 19 is facilitated. In particular, these may then be used directly as contacts.

Figure 4:
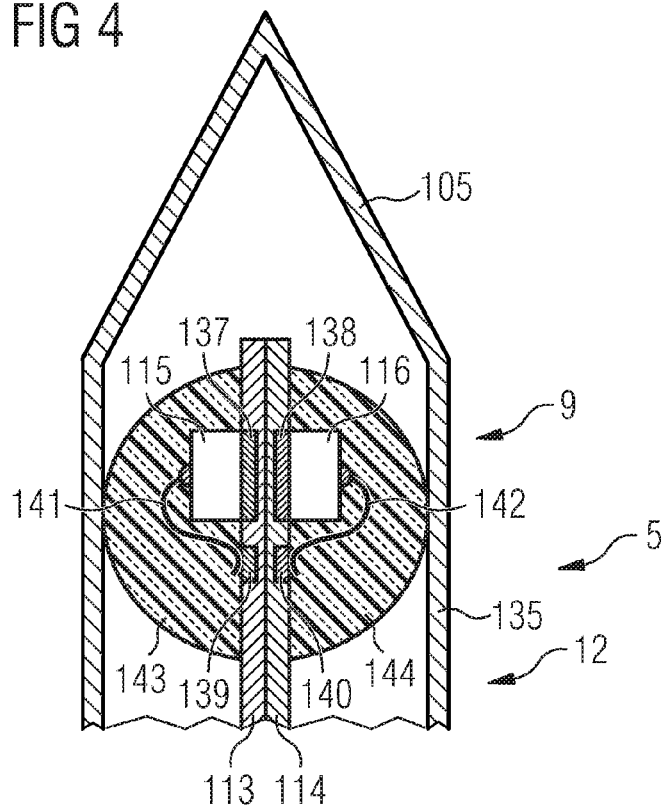
FIG. 4 shows an alternative configuration of the distal end of the endo-illuminator.

A second alternative embodiment of the small rod or small tube 5 of the endo-illuminator 1 is represented in FIG. 4. In this alternative embodiment, two flexible flat conductors strips 113, 114 are adhesively bonded together rear side on rear side. On their front sides, the conductor strips 113, 114 are equipped with first electrical contacts 137, 138 and second electrical contacts 139, 140. An LED chip 115, 116 is arranged on each first 137, 138 while electrically conductively contacting the contact. The LED chips 115, 116 are respectively connected to the second 139, 140 through bonding wires 141, 142. The LED chips 115, 116 and the respective bonding wires 141, 142 are furthermore respectively enclosed by encapsulation 143, 144, which may also contain at least one luminescent converter material.

The small rod or small tube 5 in the present alternative embodiment is configured as a small transparent plastic tube 135 with a tip 105, through the supply lead section 12 of which the conductors strips 113, 114 bonded together are fed into the distal hollow section 9. The LED chips 115, 116 are arranged on the conductor strips 113, 114 so that they lie in the distal hollow region 9 after the insertion.

Instead of in the encapsulation 143, 144, the converter material may also be applied onto the small tube 135 or introduced into the transparent wall material of the small tube 135. In respect of the options available for the introduction or application of the luminescent converter material, the comments made with reference to FIG. 3 apply similarly, although the transparent plate 45 in the present alternative embodiment is replaced by the transparent material of the small tube 135.

It should also be mentioned that not necessarily the entire small tube 135 needs to be made transparent. It is sufficient for it to be made transparent in the distal hollow section 9. The transparent material of the small tube 135 may also be configured so that it is opaque for any ultraviolet components of the excitation light of the LEDs 115, 116.

Instead of the small tube 135 described with reference to FIG. 4, however, in this alternative embodiment it is also in principle possible to employ a small tube 135 as was described with reference to FIG. 3, although a transparent circumferential surface in the region of the distal hollow section 9 is advantageous owing to the arrangement of the LED chips 115, 116.

Owing to the presence of two LED chips, this configuration allows a high brightness of the light emitted by the endo-illuminator 1. Furthermore, except for the conductor strips with LED chips arranged thereon, no components are to be fed through the supply lead section 12 of the small tube 135. The application of the LED chips 115, 116 and the encapsulation in the present alternative embodiment may be carried out in the same way as was described in the scope of the first alternative embodiment.

Figure 5:
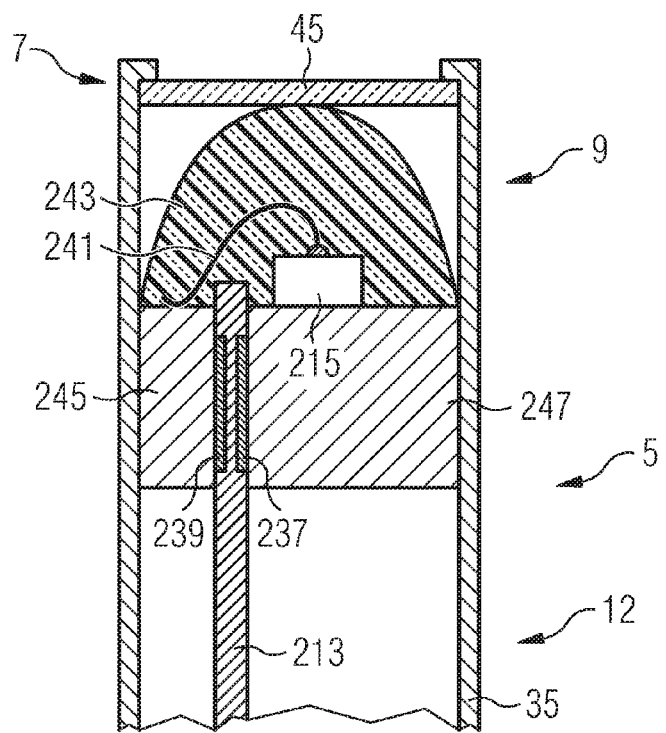
FIG. 5 shows another alternative configuration of the distal end of the endo-illuminator.

A third alternative embodiment for the small rod or small tube 5 of the endo-illuminator 1 is represented in FIG. 5. In this alternative embodiment, a small tube 35 is used in the same way as was described with reference to the first alternative embodiment. A contact arrangement 245, 247, on which an LED chip 215 is arranged, is introduced into this small tube 35. The contact arrangement 245, 247 is supplied with current through a flexible conductor strip 213, which is fed through the hollow-configured supply lead section 12. To this end, the flexible conductor strip has two electrical contacting sections 237, 239 on its distal end, which are arranged on sides of the conductor strip 213 facing away from one another.

The contact arrangement 245, 247 comprises a first electrically conductive block 247 and a second electrically conductive block 245, which are connected together and electrically insulated from one another. The conductor strip 213 extends through the contact arrangement 245, 247, specifically so that the first electrically conductive block 247 electrically contacts the first electrical contact region 237 of the conductor strip 213, while the second electrically conductive block 245 contacts the second electrical contacting section 239 of the conductor strip 213. The LED chip 215 is arranged directly on the first electrically conductive block 247 while electrically contacting it. The connection of the LED chip 215 to the second electrically conductive block 245 of the contact arrangement is established by a bonding wire 241.

The entire arrangement comprising the LED chip 215 and the bonding wire is enclosed by encapsulation 243. As in the other exemplary embodiments, the encapsulation 243 and/or the plate 45 may be provided with at least one converter material. The plate 45 may furthermore be configured so that it is opaque for ultraviolet components of the excitation light.

The production of the contact arrangement with the LED chip arranged thereon and the encapsulation may be carried out as follows: first, the blocks 245, 247 are arranged around the conductor strip 213 and adhesively bonded together. The adhesive bonding is carried out so that the blocks 245, 247 are mutually insulated. The LED chip 215 is then placed onto the first block 247 and subsequently connected to the second block 245 by means of a bonding wire 241. Encapsulation is then applied onto that side of the contact arrangement 245, 247 on which the LED chip 215 and the bonding wire 241 are located. The contact arrangement, with the LED chip 215 arranged thereon and encapsulated, may subsequently be trimmed to size so that the arrangement fits exactly into the small tube 35. Lastly, the arrangement is inserted into the small tube.

Figure 6:
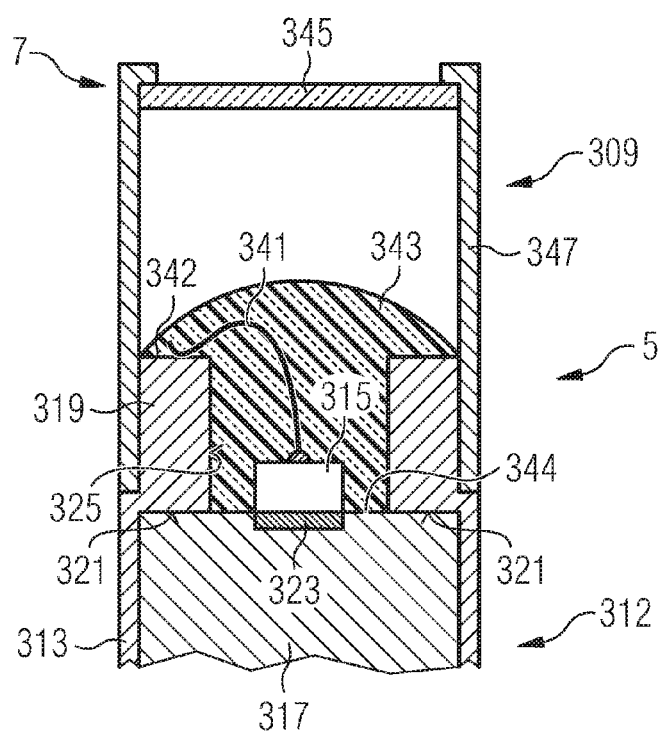
FIG. 6 shows yet another configuration of the distal end of the endo-illuminator.

A fourth alternative embodiment of the small rod or small tube 5 is represented in FIG. 6. As in FIGS. 3 to 5, the distal hollow section 309 is depicted, as is a part of the supply lead section 312. In contrast to the alternative embodiment described with reference to FIGS. 3 to 5, the supply lead section 312 of the alternative embodiment represented with reference to FIG. 6 is not in the form of a small tube, but instead in the form of a small rod. The small rod is constructed from two components, namely a cylindrical sleeve and a pin 317 inserted into the cylindrical sleeve 313 and adhesively bonded thereto.

The pin 317 and the sleeve 313 are made of an electrically conductive material, for example metal, and are electrically insulated from one another. Either the inside of the sleeve 313 or the outside of the pin 317, or both, have electrical insulation so that the two can be in mutual physical contact without an electrical contact being created. At its distal end, the sleeve 313 also has a section 319 which is reduced both in its external diameter and in its internal diameter. At the transition between the section 319 with a reduced external and internal diameter and the section without a reduced external and internal diameter, an annular bearing surface 321 is formed which serves as a stop for the pin 317.

At the distal end 344 of the pin 317, a contact spot 323 is provided in which in any event there is no insulation. An LED chip 315 is placed onto the contact spot 323 and electrically conductively connected to the contact spot 323. The LED chip 315 is furthermore connected through a bonding wire 341 to the end surface 342 of that section 319 of the sleeve 313 in which the sleeve has a reduced external and internal diameter. At least this end surface 342 has no electrical insulation. The section 319 of the sleeve 313 with a reduced external and internal diameter forms an annular contact which is arranged around a central contact, i.e. around the contact spot 323. Since it projects beyond the distal end 344 of the pin 317, its inner wall 325 delimits a recess which reaches to the distal end 344 of the pin 317. Encapsulation 343 is introduced into this recess. This configuration offers the advantage that only the recess needs to be filled with encapsulation.

In the present alternative embodiment the recess may be filled with the encapsulation, and the latter may be cured, after applying and contacting the LED chip. Instead of by curing, the encapsulation may also be held in the recess by a transparent sealing plate when the bonding wire does not contact the end surface 342 of the section 319, but instead an inner surface of the section.

In the present alternative embodiment, the distal hollow section 309 is formed by a distal sleeve 347, the internal diameter of which corresponds to the external diameter of the sleeve 313 of the supply lead section in the section with a reduced internal and external diameter. The distal sleeve 347 can therefore be fitted onto the supply lead section and, for example, adhesively bonded to it.

The distal end of the distal sleeve 347 is sealed by a transparent plate. The configuration of the plate corresponds to the configuration of the plate described with reference to FIG. 3. In respect of the arrangement of the converter material, the comments made with reference to FIG. 3 likewise apply similarly. This means that the converter material may be arranged in the encapsulation, in the plate or on the plate. Combinations thereof are also possible, including the option of providing a plurality of converter materials which differ from one another.

Figure 7:
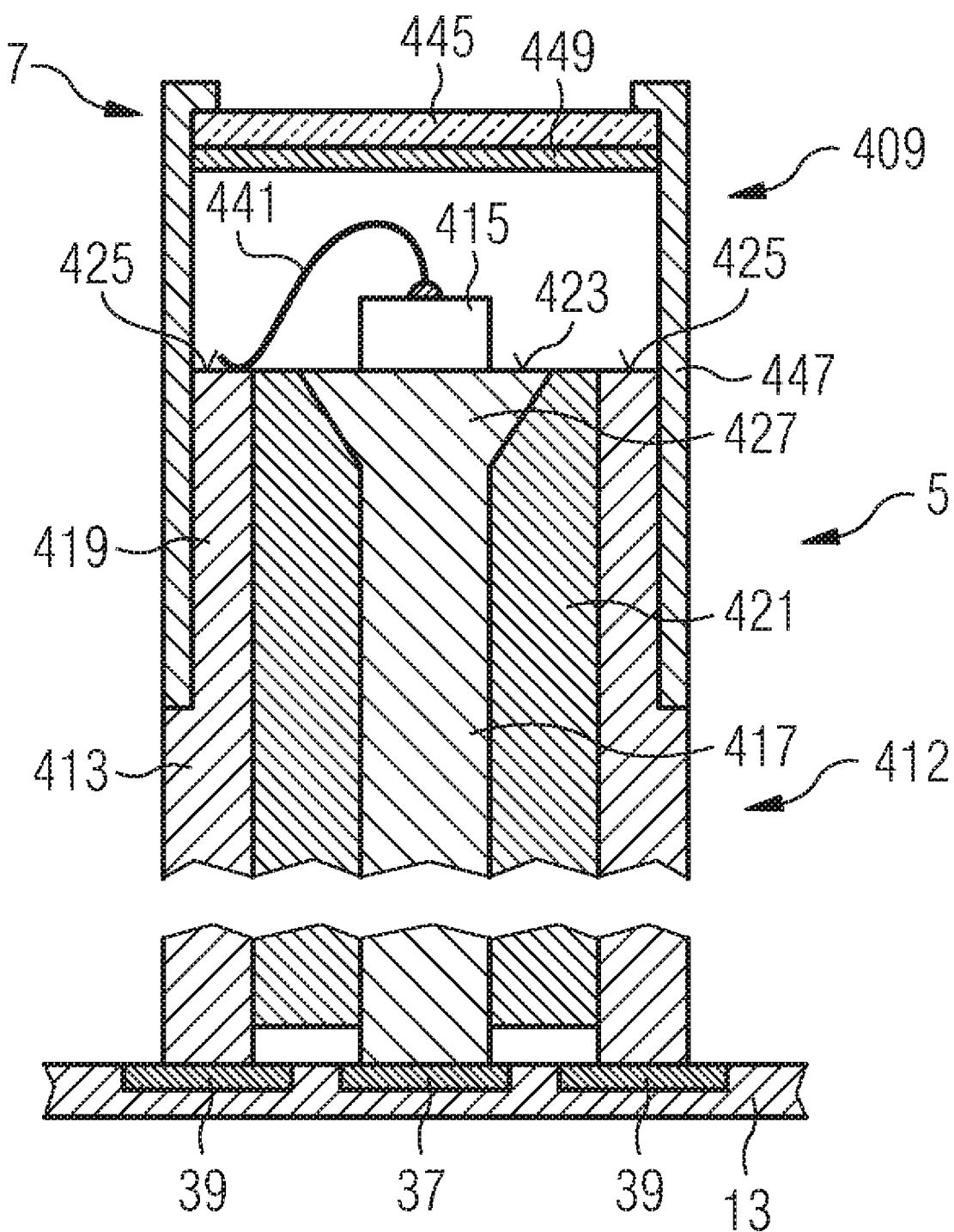
FIG. 7 lastly shows yet another alternative configuration of the distal end of the endo-illuminator.

A sixth variant of the small rod or small tube 5 of the endo-illuminator 1 is represented in FIG. 7. This variant resembles the variant described in FIG. 6 in so far as the supply lead section 412 is designed as a small rod. It comprises a cylindrical sleeve 413 and a small central rod 417 arranged at the center of the cylindrical sleeve. The external diameter of the small central rod 417 is less than the internal diameter of the sleeve 413. Between the two, an insulating material 421 is provided which holds the small rod 417 in position with respect to the sleeve 413 and ensures electrical insulation between the two. In the alternative embodiment represented, the insulating material 421 extends essentially over the entire axial length of the arrangement comprising the sleeve 413 and the small rod 417. It is however also possible to arrange insulating material 421 merely in a few axial sections, so long as stability of the arrangement and the electrical insulation are ensured.

In contrast to the alternative embodiment represented in FIG. 6, the distal end surfaces 423, 425 of the small rod 417 and of the sleeve 419, respectively, lie in a common plane. The distal end surface 423 of the small central rod 417 forms a first contact, onto which the LED chip 415 is placed with electrically conductive contacting. In order to increase the area available for placement of the LED chip 415, the small central rod 417 is broadened somewhat in its distal end region 427, but without compromising the electrical insulation from the sleeve 419. The distal end surface 425 of the sleeve 419 forms an annular second contact, to which the LED chip 415 is connected through a bonding wire 441.

The distal end of the supply lead section 412 comprises a section 419 in which the sleeve 413 has a reduced external diameter. A distal sleeve 447 is placed onto this section 419 with a reduced external diameter. The dimensions of the distal sleeve 447 selected so that its internal diameter corresponds to the external diameter of the section 419 and the external diameter of the distal sleeve 447 matches the external diameter of the sleeve 413, so as to produce an outer surface of the small tube or small rod 5 which is as smooth as possible.

The distal end of the distal sleeve 447 is sealed by a plate 445. This is transparent in the visible spectral range, and may be made opaque in the ultraviolet spectral range. The plate 445 is furthermore provided with a converter coating 449 on its side facing the interior of the sleeve. This converter coating may either consist of the converter material itself or contain the converter material. Combinations of at least two converter materials are also possible in principle.

Although the converter material is applied in the form of a coating 449 onto the inside of the plate 445 in the present alternative embodiment, it may also be applied onto the outside of the plate 445 or for example introduced into the plate 445 as doping. Furthermore, in the alternative embodiment represented in FIG. 7, it is also possible to encapsulate the LED chip 415 and the bonding wire 441. In this case, the encapsulation may also contain the converter material or the converter materials.

It should be mentioned at this point that not only can the alternative embodiment described with reference to FIG. 7 be produced without encapsulation, but also the encapsulation may be omitted from the other variants. In this case, the converter material is applied onto the plate or introduced into the plate.

In the last two alternative embodiments, which employ a distal sleeve that is fitted onto the supply lead section, it is not necessary to feed a conductive strip through a long small tube. Also, a flexible conductor strip does not need to be used in the region of the LED chip. Since the cylindrical sleeve of the supply lead section also forms a frame for the distal sleeve, it is possible to position the distal sleeve exactly with respect to the supply lead section. This is advantageous in particular whenever the inside of the plate of the distal sleeve is provided with a converter coating, since by simple means it is possible to ensure that the inside of the plate does not come in contact with any element inside the distal hollow section. Specifically, the converter coating could suffer damage in the event of contact. If the converter material has been introduced into encapsulation instead of being applied onto the plate, however, then contact between the encapsulation and the plate is not critical.

FIG. 7 furthermore shows the way in which the sleeve 413 and the central pin 417 are supplied with current. At the proximal end of the pin 417 and the sleeve 413, a flexible conductor strip 13 is arranged which comprises contacting sections 37 and 39 that are mutually insulated. The central pin 417 then contacts the contacting section 37, while the sleeve 413 contacts the contacting section 39 arranged annularly around the contacting section 37. The same type of contacting is also possible in the alternative embodiment represented with reference to FIG. 6.

In all alternative embodiments, the application of the LED chip onto contact surfaces, contacts or contact spots may be carried out by so-called die bonding. Die bonding is a so-called chip-on-board technology in which a chip is adhesively bonded, soldered, fused, welded (for example by means of ultrasound) or alloyed directly onto a substrate, in the present case the contact surfaces, without a housing, electrically conductive contact being established between the substrate and the chip.

The invention provides medical illumination units, and in particular endo-illuminators, which may also have an excitation light source at the distal end even when using small tubes or small rods with a very small external diameter. This obviates the often difficult injection of light into a light guide.

What is claimed is:

1. A medical illumination unit, which comprises:
    a rod-shaped or tubular body having a proximal end, a distal end, at least one distal hollow section that begins before the distal end and reaches the distal end, and a supply lead section that begins at the proximal end and reaches the distal hollow section, the supply lead section having a contact arrangement at its end facing the distal hollow section, the contact arrangement having a central contact and an edge contact in the form of a ring enclosing the central contact;
    an LED chip arranged in the distal hollow section of the body and being supplied with energy through the supply lead section, the LED chip being arranged on and electronically contacting the central contact and being connected to the edge contact by a bonding wire; and
    a luminescent converter material arranged between the LED chip and the distal end of the body or at the distal end of the body, the converter properties of the luminescent converter material in respect of the light emitted by the LED chip being selected so that the luminescent converter material converts light emitted by the LED chip into light with a desired wavelength distribution.

2. The medical illumination unit of claim 1, characterized in that the luminescent converter material encloses the LED chip in the form of encapsulation.

3. The medical illumination unit of claim 1, characterized in that the body is sealed at its distal end with a plate that is transparent for the desired wavelength distribution and the luminescent converter material is applied onto the plate or introduced into the plate.

4. The medical illumination unit of claim 3, characterized in that the luminescent converter material is integrated into a film applied onto the plate.

5. The medical illumination unit of claim 4, characterized in that the film is arranged on a side of the plate that faces the interior of the distal hollow section.

6. The medical illumination unit of claim 1, characterized in that at least the LED chip is encased by a sterilizable material.

7. A medical illumination unit comprising:
    a rod-shaped or tubular body having a proximal end, a distal end, at least one distal hollow section that begins before the distal end and reaches the distal end, and a supply lead section that begins at the proximal end and reaches the distal hollow section, the supply lead section having a contact arrangement at its end facing the distal hollow section, the contact arrangement having a central contact and an edge contact, the edge contact projects beyond the central contact in the direction of the distal end of the body and the edge contact encloses the central contact without a gap, electrical insulation being provided between the edge contact and the central contact; and an LED chip being arranged in the distal hollow section of the body and being supplied with energy through the supply lead section, the LED chip being arranged on and electrically contacting the central contact and being connected to the edge contact by a bonding wire, and a luminescent converter material arranged between the LED chip and the distal end of the body or at the distal end of the body, converter properties of the luminescent converter material in respect of light emitted by the LED chip are selected so that the luminescent converter material converts the light emitted by the LED chip into light with a desired wavelength distribution.

8. The medical illumination unit of claim 7, characterized in that the electrical insulation is produced by an adhesive bond between the central contact and the edge contact with an electrically insulating adhesive.

9. The medical illumination unit of claim 8, characterized in that the distal hollow section is formed by a cylindrical sleeve, into which the LED chip is introduced and which is fitted onto the supply lead section.

10. The medical illumination unit of claim 9, characterized in that the contact arrangement forms a base, onto which the sleeve is fit.

11. A medical illumination unit comprising:
a rod shaped body having a proximal end, a distal end, at least one distal hollow section that begins before the distal end and reaches the distal end and a supply lead section that begins at the proximal end and reaches the distal hollow section, the supply lead section including a small tube and first and second electrically conductive blocks electrically insulated form one another and being shaped and disposed to form a cylindrical base element, at least one flexible conductive strip fed through the small tube and having first and second electrical contacting sections, the first electrically conductive block being connected to the first contacting section of the flexible conductor strip and the second electrically conductive block being connected to the second contacting section of the flexible conductor strip;

an LED chip arranged in the distal hollow section of the body and being supplied with energy through the supply lead section; and a luminescent converter material arranged between the LED chip and the distal end of the body or at the distal end of the body, converter properties of the luminescent converter material in respect of light emitted by the LED chip being selected so that the luminescent converter material converts the light emitted by the LED chip into light with a desired wavelength distribution.

12. The medical illumination unit of claim 11, characterized in that the luminescent converter material encloses the LED chip in the form of encapsulation and the encapsulation is applied onto the cylindrical base element while covering the LED chip.

13. The medical illumination unit of claim 11, characterized in that
the at least one flexible conductor strip comprises first and second conductor strips, each of which has a front side with first and second electrical contacting sections and a rear side,
the rear sides of the two conductor strips are connected together, and
the LED chip comprising first and second LED chips respectively applied on the front sides onto the first electrical contacting sections.

14. The medical illumination unit of claim 11, characterized in that
a small rod with a flat distal end is provided, the diameter of which is less than the internal diameter of the small tube forming the supply lead section, and
the conductor strip bears on the flat distal end of the small rod in the region of the first electrical contacting section.

15. The medical illumination unit of claim 14, characterized in that the small rod has a good thermal conductivity.

* * * * *